United States Patent [19]

Turner

[11] Patent Number: 5,306,509
[45] Date of Patent: Apr. 26, 1994

[54] PREVENTION AND TREATMENT OF ORAL LESIONS

[76] Inventor: Robert E. Turner, 421 Marble Dr., Coraopolis, Pa. 15108

[21] Appl. No.: 423,500

[22] Filed: Oct. 12, 1989

Related U.S. Application Data

[63] Continuation of Ser. No. 26,738, Mar. 17, 1987, abandoned.

[51] Int. Cl.$^5$ .................... A61K 33/40; A61K 33/00
[52] U.S. Cl. .................................. 424/616; 424/717
[58] Field of Search .................. 514/835, 902; 424/53, 424/54, 616, 717

[56] References Cited

U.S. PATENT DOCUMENTS

| | | | |
|---|---|---|---|
| 4,438,102 | 3/1984 | Ganci | 424/130 |
| 4,472,373 | 9/1984 | Ryan | 424/54 |
| 4,687,663 | 8/1987 | Schaeffer | 424/52 |
| 4,748,022 | 5/1988 | Busciglio | 514/579 |

OTHER PUBLICATIONS

Scully, et al., (1989), J. Oral Pathol. Med., 18:21-7.
Whalin, et al., (1989), Oral Surg. Oral Med. Oral Pathol., 68:279-87.
Maurice, et al., (1987), The Journal of Laryngology and Otology, 917-20.
Peterson, et al., (Eds.) In Oral Complications of Cancer Chemotherapy pp. 1-12 (1983).
Dreizen, et al., (1986), Oral Sur. Oral Med. Oral Pathol., 62:650-53.
Handbook of Nonprescription Drugs (1980), pp. 317-322.
Peterson, D. E., & Sonis, S. T., "1. Epidemiology, Frequency, Distribution, Mechanisms, and Histopathology", Oral Complications of Cancer Chemotherapy, Martinus Nijhoff Publishers, the Hague/Boston/London (1987).

Primary Examiner—Zohreh A. Fay
Attorney, Agent, or Firm—Arnold, White & Durkee

[57] ABSTRACT

The present invention involves a preparation adapted for prophylaxis and treatment of oral lesions, The preparation comprises water, between about 0.1% and about 0.8% hydrogen peroxide and between about 0.1% and about 0.4% sodium bicarbonate. In more preferable embodiments of the present invention, the hydrogen peroxide is about 0.4% and the sodium bicarbonate is about 0.2%.

Additionally, a method for prophylaxis and treatment of oral lesions is included in the present invention. This method involves the step of initially providing a preparation preferably comprising water, between about 0.1% and about 0.8% hydrogen peroxide and between about 0.1% and about 0.4% sodium bicarbonate. Oral rinsing with said preparation, particularly multiple daily oral rinsing, enhances healing of oral lesions and impedes or prevents the development of oral lesions such as, for example, those frequently incident to cancer chemotherapy.

SOL also appears to be dental plaque retardant. The clinical crowns of the patients teeth appear to be free of debris during the periods of significant myelosuppression when dental flossing and toothbrushing should not and were not performed.

13 Claims, No Drawings

PREVENTION AND TREATMENT OF ORAL LESIONS

This is a continuation of copending application Ser. No. 07/026,738 filed on Mar. 17, 1987 now abandoned.

BACKGROUND OF THE INVENTION

The present invention relates to a composition and method of prophylaxis and treatment for oral mucosal lesions. Oral lesions of various forms may develop in many circumstances and conditions. These forms of oral lesions include, for example, ulcerations, infections, stomatitis and vesiculo-bullous lesions. Among the most acute of these oral lesions are those typically occurring as an incident to cancer chemotherapy. These chemotherapy-related lesions may be so painful and severe as to force cessation of the chemotherapy, as well as eating and drinking, which may interfere with medical treatment. The lack of a consistent, effective and convenient method of prophylaxis and treatment for such oral lesions has too long been a therapeutic handicap.

Certain antineoplastic drugs have well documented direct and indirect stomatotoxicity. The direct toxicity is characterized by the interruption of the migrating, maturing squamous cells from the basal cell layer to the oral mucosal surface. As this normal progression is attenuated and desquamation of surface cells continues, it may be clinically manifested as oral mucosal ulcerations. Acute and severe pain may be associated with this ulcerative process at it's developmental peak. Patients have discontinued their chemotherapy due to this complication. Such cessation means that the full chemotherapy protocol cannot be delivered and thus, the patient may not be provided the best therapeutic effect. Control or cure of the cancer may be lost. The patient and family are then placed in an emotional struggle between gaining relief from the oral pain and simultaneously realizing that in doing so the cancer may continue to progress.

The indirect stomatotoxic effects are related to alteration of the hematologic status through myelosupression and the patient's subsequent decreased ability to resist infections and hemorrhage. Oral infections increase the overall morbidity of cancer chemotherapy. If these infections are not discovered early and treated aggressively, they may be lethal following their systemic dissemination. Oral hemorrhaging may occur spontaneously and be profuse. Such incidents are terribly distressful to the patient, family and the professional care team. Fatal exsanguination has been reported.

Currently, antineoplastic drug therapy is being used with 40% of cancer patients either as a single treatment modality or as part of multi-modal therapy (chemotherapy, surgery, radiation). Some cancers respond well to single agent chemotherapy and others are treated with several agents in combination. New combinations and single agents are used in investigational clinical trials. The oral toxicity must be identified for all of these new agents and new combinations. Data show that nearly 50% of all individuals receiving chemotherapy will develop oral complication. These complication include stomatitis, infection and hemorrhage. Of this 50% incidence rate, 33% will develop one complication, 10% two complications and 3-4% will develop all three.

There is a plethora of scientific reports describing the multiple and varied oral complications as sequelae to cancer chemotherapy. Great detail has been used to describe these clinical entities. To a lesser degree, the scientific literature offers explanations for the pathogenesis of these oral lesions. Treatment protocols for these sequelae are more sparse and varied. Their development seems to be more empiric than scientific. An extensive literature search and a preliminary survey of some of the major cancer treatment centers in North America indicate that no treatment is presently available to prevent or significantly attenuate these oral complications. Clearly, there is a need for a proven, safe, comfortable and effective method and material to address this widespread and difficult problem.

SUMMARY OF THE INVENTION

The present invention involves a preparation adapted for prophylaxis and treatment of oral lesions. The preparation comprises water, between about 0.1% and about 0.8% hydrogen peroxide and between about 0.1% and about 0.4% sodium bicarbonate. To produce such a preparation adapted for the prophylaxis and treatment of oral lesions most preferably involves dissolving hydrogen peroxide and sodium bicarbonate in an aqueous solution to produce a preparation having between about 0.1% and about 0.8% hydrogen peroxide and between about 0.1% and about 0.4% sodium bicarbonate. In more preferable embodiments of the present invention, the hydrogen peroxide is about 0.4% and the sodium bicarbonate is about 0.2%.

Additionally, a method for prophylaxis and treatment of oral lesions is included in the present invention. This method involves the step of initially providing a preparation preferably comprising water, between about 0.1% and about 0.8% hydrogen peroxide and between about 0.1% and about 0.4% sodium bicarbonate. Oral rinsing with said preparation, particularly multiple daily oral rinsing, enhances healing or oral lesions and impedes or prevents the development of oral lesions such as, for example, those frequently incident to cancer chemotherapy.

In certain preferred embodiments, the preparation for prophylaxis and treatment of the present invention is defined further as comprising alcohol and cetylpyridinium chloride, most preferably between about 0.5% and about 2.0% ethyl alcohol and between about 0.0003% and about 0.05% cetylpyridinium chloride. The preparation of the present invention may contain between about 20% and about 50% isotonic saline solution. In a preferred embodiment, the aqueous preparation of the present invention adapted for prophylaxis and treatment of oral lesions such as those often incident to cancer chemotherapy, comprise about 0.0003% cetylpyridinium chloride, about 1% ethyl alcohol, about 0.4% hydrogen peroxide, about 0.2% sodium bicarbonate and about 30% isotonic saline. In usage the preparation is used for oral rinsing on a daily multiple basis.

DESCRIPTION OF THE PREFERRED EMBODIMENT

The present invention involves the prophylaxis and treatment of oral lesions with a mouthwash comprising hydrogen peroxide and sodium bicarbonate.

The following examples involving patients undergoing cancer chemotherapy are presented to describe preferred embodiments and utilities of the present invention and are not meant to limit the present invention unless otherwise stated in the claims appended hereto.

EXAMPLE I

STANDARD ORAL LAVAGE

Standard oral lavage (SOL) is a therapeutic oral rinse of the present invention that has been developed for individuals with oral soft tissue problems. These individuals are most clearly exemplified as medical oncology patients subject to chemotherapy who are likely to be the greatest beneficiaries of SOL treatment. SOL had it's genesis from an understanding of oral physiology and alternations of this physiology during and after chemotherapy treatments.

In the preferred embodiment therapeutically utilized herein, the following SOL was used.

100 ml CEPACOL mouthwash (Lakeside Pharmaceuticals, Cincinatti, Ohio)
200 ml 3% hydrogen peroxide
400 ml normal saline
800 ml sterile water
3360 mg sodium bicarbonate the formula was packaged in a clear 1½ liter plastic jug, then inserted in an amber plastic bag for storage. The amber bag was to impede hydrogen peroxide from being deactivated by light.

Pertinent to a description of the clinical efficacy of (SOL) the following examples are summaries of three patients who were being subjected to cancer chemotherapy. These patients responded favorably to SOL and developed minimal or no stomatitis.

EXAMPLE II

M. J. was a 32 year old white female patient having a diagnosis of acute monocytic leukemia. She was treated with a standard remission-induction course of chemotherapy consisting of the following: Ara-C (170 mg per day) for seven days as a continuous intravenous infusion and Adriamycin (76 mg per day) for three days, intravenous push. She developed a severe stomatitis which required an intravenous morphine drip to manage pain. There was severe ulceration of the labial and buccal mucous membranes which hemorrhaged sporadically and without provocation. The ventral surfaces of the tongue and the anterior floor of the mouth were similarly involved. Crenation of the tongue, due to fluid retention, produced additional traumatic ulcerations of its periphery from the base on the right side circumferentially to the left base. The uvula, soft palate, tonsillar pillars and the posterior oropharynx had multiple ulcerative lesions. Many of these oral lesions presented with pseudomembranes. Gingival hemorrhaging was bothersome at times. *Candida albicans* became a complicating component as an opportunistic infection.

SOL was minimally used as an oral rinse every two hours while the patient was awake and twice during the night. M. J. was instructed to rinse with two to three ounces of SOL as described above and more frequently, if desired. A topical antifungal rinse was employed following meals and at bedtime to prevent and treat Candida.

Through the use of SOL and careful clinical surveillance, the patient's initial severe stomatitis was resolved in six days during a period of pancytopenia. Since the remission-induction chemotherapy the patient received seven more courses of induction and consolidation chemotherapy. Several of these courses were high dose Ara-C and L-asparaginase. The only oral reaction noted was with sequential high dose Ara-C courses of a one week duration. With this therapy, accompanied by SOL treatment, one oral ulcer developed with each week of treatment; these ulcers measuring about one millimeter in diameter. The patient was free from any other oral pathology.

EXAMPLE III

Another patient was W. W., a 49 year old white male with advanced colorectal cancer. This patient with Duke's classification C adenocarcinoma of the rectum, was treated surgically and with post-operative radiotherapy. Recurrence of this cancer was managed with high dose 5-fluorouracil administered as continuous intravenous infusion for five days. This regimen produced a moderately severe stomatitis that involved the labial and buccal mucosae and the latero-ventral surfaces of the tongue. It must be noted that this patient had multiple missing and cariously diseased teeth. Periodontally, these teeth showed significant bone loss.

Treatment of this 5-fluorouracil-induced stomatitis was performed with SOL in the same protocol described in Example II. Subsequent courses of 5-fluorouracil were administered to this patient using the identical dose and route of administration but accompanied with SOL therapy and no stomatitis was found to develop with steadily increasing CEA levels.

Patient W. W. was not totally compliant with the oral care and smoked rather heavily, (two to three packs of Camels per day). Tooth brushing and the use of dental floss were never part of the patient's health habits.

EXAMPLE IV

Another patient, J. L., was a 23 year old while male with a diagnosis of acute myeloblastic leukemia. This patient received a standard remission-induction chemotherapy regimen consisting of the following: Ara-C (190 mg per day) for seven days as a continuous intravenous infusion and Daunomycin (85 mg per day) for three days intravenous push.

As this chemotherapy quite consistently produces stomatitis, the patient was managed with the SOL protocol described in Example III. Only slight inflammation of the maxillary facial posterior gingivae on the left was noted. No oral ulcerations were seen. There were numerous consolidation treatments with m-AMSA/Ara-C and AraC/Daunomycin. Several of these regimen were high dose. No stomatitis developed in this patient during or after these treatments.

SOL has been used to resolve, attenuate and prevent stomatitis in patients with sold and non-solid malignancies, all of which were treated with currently accepted chemotherapy protocols. Stomatitis is a reported significant side-effect in all of these treatment schedules. SOL not only performed well as a clinically effective agent for stomatitis but appeared to have a rather pronounced anti-plaque potential. During the severe and prolonged myelosuppression following chemotherapy for leukemia, these patients should not and did not perform any dental flossing or toothbrushing. This oral physiotherapy abstinence continued until the patients became hematologically stable so that flossing and toothbrushing would not produce any gingival hemorrhaging or life-threatening bacteremia/septicemia. The clinical crowns of the teeth, in these patients, remained clean and shiny during the severe neutropenic periods. None of these patients with natural dentition developed any significant gingival complications. Although these examples involve patients subject to cancer chemotherapy, the SOL treatment should have application for any individuals susceptible or subject to stomatitis-relates oral lesions.

Changes may be made in the elements and components described herein or in the steps or the sequence of steps of the method described herein without departing from the concept and scope of the invention as defined in the following claims.

What is claimed is:

1. A method for prophylaxis and treatment of oral lesions incident to use of a chemotherapeutic agent, the method comprising the steps of:

identifying a patient with a susceptibility to or already having oral lesions incident use of a chemotherapeutic agent; and orally rinsing said patient multiple times per day for a period of time at least as long as the chemotherapeutic agent is administered, and until the patient is hematologically competent, with a premixed aqueous solution consisting essentially of between about 0.1% and about 0.8% hydrogen peroxide, and between about 0.1% and about 0.4% sodium bicarbonate, wherein the premixed aqueous solution is therapeutically effective for at least 6 days after mixture stored in a light impeding container.

2. A method for preventing oral lesions incident use of a chemotherapeutic agent, the method comprising the steps of:

identifying a patient with a susceptibility to oral lesions incident use of a chemotherapeutic agent; and orally rinsing said patient multiple times per day for a period of time at least as long as the chemotherapeutic agent is administered, and until the patient is hematologically competent, with a premixed aqueous solution comprising between about 0.1% and about 0.8% hydrogen peroxide, and between about 0.1% and about 0.4% sodium bicarbonate, wherein the premixed aqueous solution is therapeutically effective for at least 6 days stored in a light impeding container.

3. A method for treating oral lesions incident use of a chemotherapeutic agent, the method comprising the steps of:

identifying a patient with a susceptibility to, or with oral lesions incident to use of, a chemotherapeutic agent; and orally rinsing said patient multiple times per day for a period of time at least as long as chemotherapy is conducted, and until the patient is hematologically competent, with a premixed aqueous solution consisting essentially of between about 0.1% and about 0.8% hydrogen peroxide, and between about 0.1% and about 0.4% sodium bicarbonate, wherein the premixed aqueous solution is therapeutically effective for at least 6 days after mixture stored in a light impeding container.

4. The method of claim 1, 2 or 3 wherein the aqueous solution comprises between about 20% and about 50% isotonic saline solution.

5. The method of claim 1, 2 or 3 wherein the aqueous solution comprises about 0.4% hydrogen peroxide.

6. The method of claim 1, 2 or 3 wherein the aqueous solution, comprises ethyl alcohol.

7. The method of claim 1, 2 or 3 wherein the aqueous solution comprises about 0.2% sodium bicarbonate.

8. The method of claim 1, 2 or 3 wherein the aqueous solution comprises between about 0.5% and about 2.0% ethyl alcohol.

9. The method of claim 1, 2 or 3 wherein the aqueous solution consists essentially of about 0.4% hydrogen peroxide and about 0.2% sodium bicarbonate.

10. The method of claim 1, 2 or 3, wherein the chemotherapeutic agent is an orally toxic chemotherapeutic agent Ara-C, 5-fluorouracil, daunomycin, methotrexate, m-AMSA, cis-platinum, bleomycin or cytosine arabinoside.

11. The method of claim 1, 2 or 3 wherein the premixed aqueous solution is stored in an amber-colored light impeding container.

12. A premixed aqueous formulation for the treatment of oral lesions consisting essentially of between about 0.1% and about 0.8% hydrogen peroxide and between about 0.1% and about 0.4% sodium bicarbonate, together in sterile saline or sterile water, said premixed aqueous formulation being therapeutically effective for treating oral lesions for at least 6 days stored in a light impeding container.

13. The premixed aqueous formulation of claim 12 wherein the formulation has a pH of between 8.2-8.4 and is stored in an amber-colored light impeding container.

* * * * *